United States Patent
Lim et al.

(10) Patent No.: US 9,163,929 B2
(45) Date of Patent: Oct. 20, 2015

(54) TOMOGRAPHIC IMAGE GENERATION APPARATUS HAVING MODULATION AND CORRECTION DEVICE AND METHOD OF OPERATING THE SAME

(71) Applicants: Samsung Electronics Co., Ltd., Suwon-si (KR); Korea Advanced Institute of Science and Technology, Daejeon (KR)

(72) Inventors: Jae-guyn Lim, Seongnam-si (KR); Jae-duck Jang, Daejeon (KR); Hyun Choi, Seoul (KR); Yong-keun Park, Daejeon (KR); Hyeon-seung Yu, Daejeon (KR); Seong-deok Lee, Seongnam-si (KR); Woo-young Jang, Seongnam-si (KR)

(73) Assignees: Samsung Electronics Co., Ltd., Suwon-si (KR); Korea Advanced Institute of Science and Technology, Daejeon (KR)

( * ) Notice: Subject to any disclaimer, the term of this patent is extended or adjusted under 35 U.S.C. 154(b) by 168 days.

(21) Appl. No.: 13/898,144

(22) Filed: May 20, 2013

(65) Prior Publication Data

US 2014/0055789 A1   Feb. 27, 2014

(30) Foreign Application Priority Data

Aug. 23, 2012  (KR) .................. 10-2012-0092398
Nov. 14, 2012  (KR) .................. 10-2012-0129100

(51) Int. Cl.
*G01B 9/02*   (2006.01)
*A61B 5/00*   (2006.01)

(52) U.S. Cl.
CPC .......... *G01B 9/02091* (2013.01); *A61B 5/0066* (2013.01)

(58) Field of Classification Search
CPC ........... G01B 9/02091; G01B 9/02062; A61B 5/0066; A61B 3/102
USPC .................................... 356/479, 497
See application file for complete search history.

(56) References Cited

U.S. PATENT DOCUMENTS 6,859,275 B2   2/2005  Fateley et al.
6,914,711 B2   7/2005  Novotny et al.
(Continued)

FOREIGN PATENT DOCUMENTS

GB    2 417 789 A    3/2006
JP    2007-199572 A   8/2007
(Continued)

OTHER PUBLICATIONS

I.M. Vellekoop et al., "Phase control algorithms for focusing light through turbid media, " *Optics Communications*, vol. 281, No. 11, Jun. 1, 2008, pp. 3071-3080.
(Continued)

*Primary Examiner* — Tarifur Chowdhury
*Assistant Examiner* — Jonathan Cook
(74) *Attorney, Agent, or Firm* — NSIP Law (57) ABSTRACT

A tomographic image generation apparatus includes a light source unit configured to emit light to be used for scanning an object; an optical control unit configured to control a direction of propagation of light; an optical coupler configured to divide and combine incident light; a plurality of optical systems optically connected to the optical coupler; and a modulation and correction device configured to modulate and correct the light to be used for scanning the object. The modulation and correction device may be disposed between the optical control unit and the optical coupler, or may be included in an optical system that irradiates light onto the object among the plurality of optical systems. The modulation and correction device may only modulate light that is reflected to the object.

22 Claims, 6 Drawing Sheets

(56) References Cited

U.S. PATENT DOCUMENTS

| | | | |
|---|---|---|---|
| 8,096,665 B2 | 1/2012 | Bellis et al. | |
| 2003/0053026 A1* | 3/2003 | Roorda | 351/206 |
| 2006/0058682 A1 | 3/2006 | Miller et al. | |
| 2007/0038040 A1 | 2/2007 | Cense et al. | |
| 2007/0046948 A1 | 3/2007 | Podoleanu et al. | |
| 2008/0002211 A1 | 1/2008 | Park et al. | |
| 2009/0009885 A1 | 1/2009 | Smith et al. | |
| 2010/0295984 A1 | 11/2010 | Neidrich | |
| 2011/0090499 A1* | 4/2011 | Van Der Mark | 356/327 |
| 2011/0096293 A1* | 4/2011 | Hirose et al. | 351/206 |
| 2012/0038885 A1 | 2/2012 | Cense et al. | |

FOREIGN PATENT DOCUMENTS

| | | |
|---|---|---|
| JP | 2009-3173 A | 1/2009 |
| KR | 10-2008-0014738 A | 2/2008 |
| KR | 10-2011-0036849 A | 4/2011 |
| WO | WO 2010/014164 A1 | 2/2010 |

OTHER PUBLICATIONS

Extended European Search Report issued on Nov. 18, 2013, in counterpart European Application No. 13181509.4 (7 pages, in English).

* cited by examiner

TOMOGRAPHIC IMAGE GENERATION APPARATUS HAVING MODULATION AND CORRECTION DEVICE AND METHOD OF OPERATING THE SAME

CROSS-REFERENCE TO RELATED APPLICATIONS

This application claims the benefit of Korean Patent Applications No. 10-2012-0092398 filed on Aug. 23, 2012, and No. 10-2012-0129100 filed on Nov. 14, 2012, in the Korean Intellectual Property Office, the disclosures of which are incorporated herein by reference in their entirety.

BACKGROUND

1. Field

This application relates to tomographic image generation apparatuses having a modulation and correction device that can generate a more precise tomographic image by increasing a penetration depth in an object and a magnitude of a signal generated from the object, and methods of operating the same.

2. Description of Related Art

Tomography is a technique for capturing a tomographic image of an object using a penetrating wave. Tomography is used in many fields. Therefore, the demand for obtaining more precise tomographic images is also increased. In particular, in medical fields that are directly related to human life, a technique for generating a more precise tomographic image is an important issue.

SUMMARY

In one general aspect, a tomographic image generation apparatus includes a light source unit configured to emit light to be used for scanning an object; an optical control unit configured to control a direction of propagation of light; an optical coupler configured to divide and combine incident light; a plurality of optical systems optically connected to the optical coupler; and a modulation and correction device configured to modulate and correct the light to be used for scanning the object.

The modulation and correction device may be disposed between the optical control unit and the optical coupler.

The plurality of optical systems may include a first optical system configured to provide a reference light; and a second optical system configured to irradiate light to the object.

The plurality of optical systems may further include a third optical system configured to receive an interference pattern of light generated from the first optical system and light generated from the second optical system.

The second optical system may include the modulation and correction device.

The second optical system may include a spatial light modulator (SLM) configured to modulate light that enters from the optical coupler; a galvanometer configured to reflect light that enters from the SLM to the object and reflect light that enters from the object to the SLM; and an object lens configured to focus light that enters from the galvanometer onto the object.

The modulation and correction device may be disposed between the second optical system and the optical coupler.

The modulation and correction device may be disposed between the optical coupler and the first optical system.

The modulation and correction device may include an optical modulator configured to modulate only light that enters from the optical coupler; and a grating configured to remove diffracted light unnecessarily generated in the optical modulator.

The grating may have a groove density that is the same as a groove density of the optical modulator.

The grating may have a groove density that is different than a groove density of the optical modulator; and the modulation and correction device may further include a first lens and a second lens disposed between the optical modulator and the grating and configured to compensate for the difference in groove density between the optical modulator and the grating.

In the optical modulator, a reflection region of light that enters from the optical coupler may be different from a reflection region of light that enters from the object.

The optical modulator may be a digital micro-mirror device (DMD) or a spatial light modulator (SLM).

The modulation and correction device may include an optical modulator configured to modulate light that enters from the optical coupler; and a grating configured to remove diffracted light unnecessarily generated from the optical modulator.

The grating may have a groove density that is different from a groove density of the optical modulator; and the modulation and correction device may further include a first lens and a second lens disposed between the optical modulator and the grating and configured to compensate for the difference in groove density between the optical modulator and the grating.

The first optical system may include a lens corresponding to the first and second lenses.

The modulation and correction device may be disposed between the optical coupler and the object.

The optical coupler may be replaced by a beam splitter.

The tomographic image generation apparatus may be an optical coherence tomography apparatus or an optical coherence tomography microscope.

In another general aspect, a method of operating a tomographic image generation apparatus includes a light source unit configured to emit light to be used for scanning an object; an optical control unit configured to control a direction of propagation of light; an optical coupler configured to divide and combine incident light; a plurality of optical systems optically connected to the optical coupler; and a modulation and correction device configured to modulate and correct the light to be used for scanning the object and including an optical modulator; the method including performing an optical modulation operation with respect to only light that is reflected to the object using the optical modulator of the modulation and correction device.

Light that enters the optical modulator from the optical coupler may be incident to a first region of the optical modulator; light that enters the optical modulator from the object may be incident to a second region of the optical modulator; the first and second regions may be separated from each other; and an optical modulation operation may be performed only in the first region.

The modulation and correction device may be disposed between the optical control unit and the optical coupler.

The modulation and correction device may be disposed between the optical coupler and the object.

The tomographic image generation apparatus may include a beam splitter instead of the optical coupler.

Other features and aspects will be apparent from the following detailed description, the drawings, and the claims.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

Figure 1:
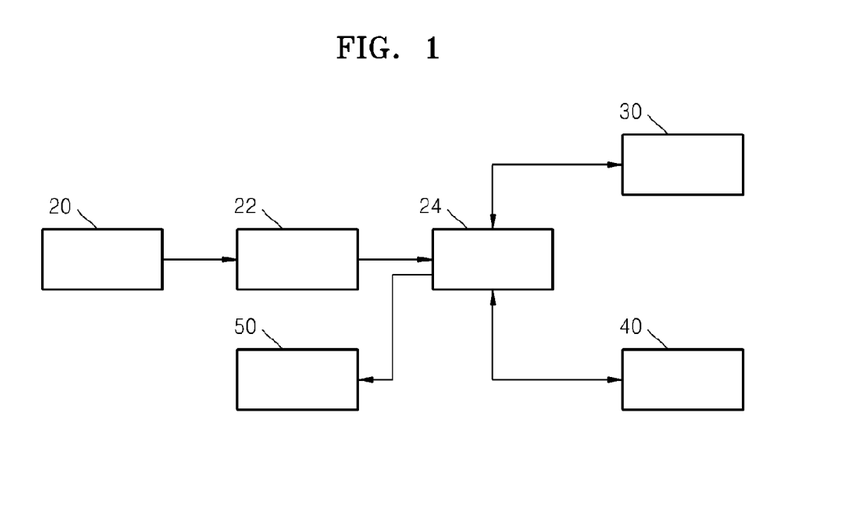
FIG. 1 is a block diagram of an example of a configuration of a tomographic image generation apparatus.

FIG. 1 is a block diagram of an example of a configuration of a tomographic image generation apparatus.

Referring to FIG. 1, the apparatus includes a light source unit 20, a light control unit 22, and an optical coupler 24. Also, the apparatus includes first, second, and third optical systems 30, 40, and 50 connected to the optical coupler 24. The light source unit 20 emits light to be irradiated to an object whose tomographic image is to be captured. The light source unit 20 may emit coherent light. The light source unit 20 may include a light source that emits coherent light.

As another example, the light source unit 20 may include a first light source that emits non-coherent light, and an element that transforms the non-coherent light emitted from the first light source to coherent light.

A light source that is included in the light source unit 20 and emits coherent light may be, for example, a laser diode. The first light source that is included in the light source unit 20 and emits non-coherent light may be, for example, a light-emitting diode (LED). The element that transforms non-coherent light to coherent light may be located between the light source unit 20 and the light control unit 22. Light emitted from the light source unit 20 may have a center wavelength of, for example, 1025 nm, and may have a predetermined bandwidth with the center wavelength at the center of the predetermined bandwidth. The light control unit 22 may be a device that prevents the light emitted from the light source unit 20 from re-entering the light source unit 20 by being reflected by other constituent elements of the apparatus. The optical coupler 24 may be a device that transmits light to the first and second optical systems 30 and 40 by dividing light emitted from the light source unit 20. Also, the optical coupler 24 may be a device that transmits light to the third optical system 50 by combining light entering from the first and second optical systems 30 and 40. The splitting ratio of light divided in the optical coupler 24 to the first and second optical systems 30 and 40 may be different from each other. For example, in the optical coupler 24, an amount of light divided to the second optical system 40 may be greater than an amount of light divided to the first optical system 30. The first optical system 30 may be an optical system that receives light from the optical coupler 24 and reflects the light to the optical coupler 24. This optical system may be connected to the optical coupler 24. The first optical system 30 may provide a reference light with respect to light to be processed in the second optical system 40. Accordingly, the first optical system 30 may be a reference optical system with respect to the second optical system 40. The second optical system 40 receives light from the optical coupler 24. The second optical system 40 may be connected to the optical coupler 24. The second optical system 40 modulates an amplitude or a frequency of light received from the optical coupler 24, and then irradiates the modulated light onto an object whose tomographic image is to be captured. The second optical system 40 transmits light reflected by the object to the optical coupler 24. The object whose tomographic image is to be captured may be an organism that includes a plurality of cells. The object whose tomographic image is to be captured may be a living organ, for example, a skin of a living organ or a surface (an epidermis) of an organ. The third optical system 50 may be a device that is connected to the optical coupler 24 and generates tomography information of an organ of the object. The tomography information may be obtained from a combination of lights received from the first and second optical systems 30 and 40 through the optical coupler 24. Additionally, the third optical system 50 may record tomography information of an organ of an object whose tomographic image is to be captured. Configurations of the first through third optical systems 30, 40, and 50 will be described below.

Figure 2A:
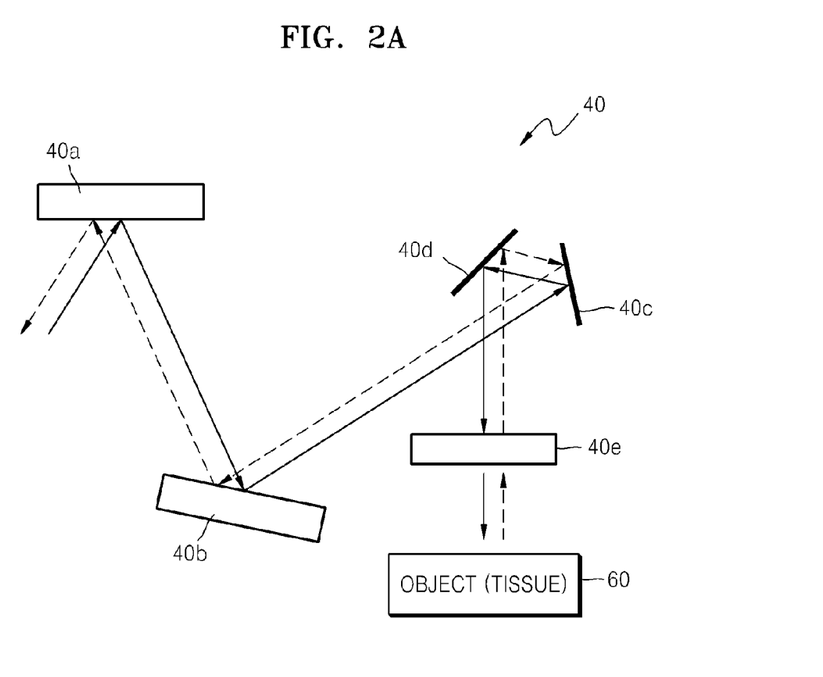
FIG. 2A is a cross-sectional view of an example of a configuration of a second optical system of FIG. 1.
Figure 2B:
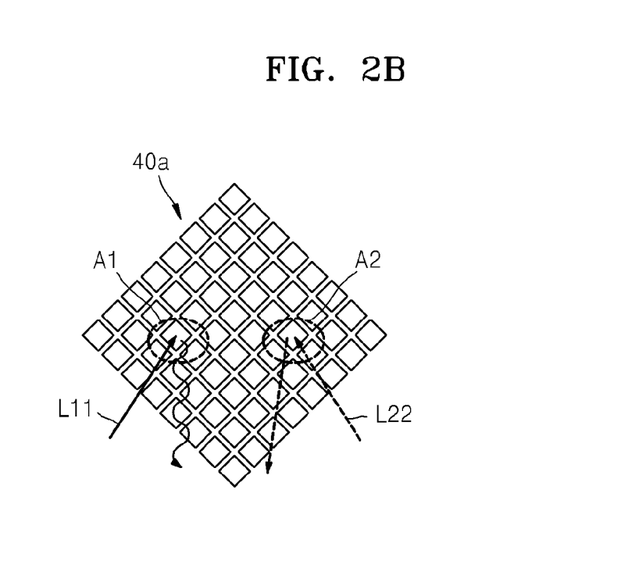
FIG. 2B is a perspective view showing an example of a case when a region where light entering from an optical modulator to an optical coupler is reflected and a region where light entering from an object whose image is to be captured is reflected are different.

FIG. 2A is a cross-sectional view of an example of a configuration of the second optical system 40 of FIG. 1. FIG. 2B is a perspective view showing an example of a case when a region where light entering from an optical modulator 40a to the optical coupler 24 is reflected and a region where light entering from an object 60 whose tomographic image is to be captured is reflected are different.

Referring to FIG. 2A, the second optical system 40 includes the optical modulator 40a, a first grating 40b, first and second mirrors 40c and 40d, and a first object lens 40e. The optical modulator 40a and the first grating 40b may constitute a modulation and correction device. The first and second mirrors 40c and 40d may be disposed at a predetermined angle relative to each other, and may rotate within a pre-set rotation range with respect to a given center axis. The first and second mirrors 40c and 40d may constitute a galvanometer. At this point, a driving element, for example, a rotation motor (not shown) for driving the first and second mirrors 40c and 40d may be further included. The optical modulator 40a may be a device that modulates an amplitude or a frequency of light (the solid lines) entering from the optical coupler 24. The optical modulator 40*a* may include a plurality of pixels. The pixels may form an array, and the pixels may have gaps of, for example, approximately 10 µm. The optical modulator 40*a* may correspond to a grating having a plurality of groves. When a gap between the pixels is approximately 10 µm, the optical modulator 40*a* may have a groove density corresponding to 100. The groove density denotes a slit density (a number of slits per mm). Each of the pixels performs as a wave source. A wavefront of light (a plane wave) that enters the optical modulator 40*a* may be newly configured by controlling the pixels of the optical modulator 40*a*. Accordingly, light (the solid line) reflected at the optical modulator 40*a* may have a wavefront that is different from that of light that enters the optical modulator 40*a*. That is, light reflected at the optical modulator 40*a* may have a pattern that is different from that of light that enters the optical modulator 40*a*. For the optical modulation as described above, pixels located on a region where light enters the optical modulator 40*a* may be controlled, and through this control, the pattern of incident light may be modulated to be a desired pattern.

The optical modulator 40*a* does not perform an optical modulation operation with respect to light (the dashed line) reflected by the object 60. The optical modulator 40*a* performs an optical modulation operation with respect to only light (the solid line) that enters from the optical coupler 24.

More specifically, as depicted in FIG. 2B, light L11 incident to the optical modulator 40*a* from the optical coupler 24 enters a first region A1 of the optical modulator 40*a*. The first region A1 is a region where an optical modulation operation is performed. Accordingly, the light L11 incident to the optical modulator 40*a* from the optical coupler 24 is modulated and is reflected to the first grating 40*b*.

Light L22 incident to the optical modulator 40*a* from the object 60 enters a second region A2 of the optical modulator 40*a*. The second region A2 is separated from the first region A1. The second region A2 is a region where an optical modulation operation is not performed. Accordingly, the light L22 incident to the optical modulator 40*a* from the object 60 is reflected to the optical coupler 24 without any optical modulation.

The optical modulator 40*a* may be, for example, a digital micro-mirror device (DMD) or a spatial light modulator (SLM). The DMD includes a plurality of mirrors and each of the micro-mirrors may perform as a pixel. Since the optical modulator 40*a* may perform as a grating, a large amount of diffracted light may be generated from the optical modulator 40*a*. A specific diffracted light of the diffracted lights, for example, a fourth diffracted light, is used for obtaining a tomographic image of the object 60. Accordingly, diffracted lights that are not used for obtaining a tomographic image of the object 60 may be diffracted light unnecessarily generated, and to remove the diffracted light unnecessarily generated, the second optical system 40 includes the first grating 40*b*. The first grating 40*b* may have a groove density (a slit density) that is the same as that of the optical modulator 40*a*. Therefore, a specific diffracted light generated from the optical modulator 40*a* enters the object 60 and the diffracted light unnecessarily generated may be removed. Thus, light may be penetrated into a deeper region of the object 60, and thus a clear tomographic image of a corresponding region may be obtained. The first mirror 40*c* reflects light that is incident from the first grating 40*b* to the second mirror 40*d*. An incidence angle of light incident to the second mirror 40*d* may be controlled by controlling the rotation angle of the first mirror 40*c*. The second mirror 40*d* reflects light that enters from the first mirror 40*c* to the object 60. The reflection angle of light reflected at the second mirror 40*d* may be controlled by controlling the rotation angle of the second mirror 40*d*, and, as a result, the incidence angle of light (the solid line) incident to the object 60 may be controlled. The incidence angle of light incident to the object 60 may be controlled by controlling the rotation angles of the first and second mirrors 40*c* and 40*d*. Therefore, optical scanning of light with respect to the object 60 may be performed by controlling the rotation angles of the first and second mirrors 40*c* and 40*d*. Light (the solid line) reflected at the second mirror 40*d* is focused on the object 60 through the first object lens 40*e*. Light (the dashed line) reflected by the object 60 includes tomographic image information of a scanned region of the object 60 and enters the optical coupler 24 sequentially through the first object lens 40*e*, the second mirror 40*d*, the first mirror 40*c*, the first grating 40*b*, and the optical modulator 40*a*. Interference occurs between the light that enters the optical coupler 24 from the optical modulator 40*a* and a reference light that enters from the first optical system 30, and a result of the interference (an interference pattern) is transmitted to the third optical system 50.

Figure 3:
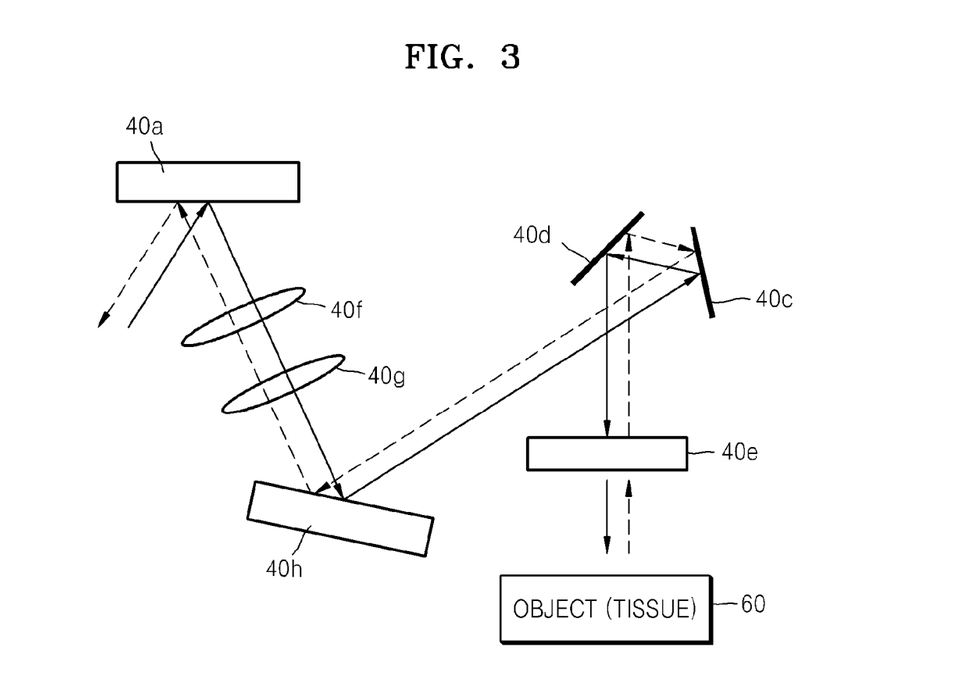
FIG. 3 is a cross-sectional view of another example of a configuration of a second optical system of FIG. 1.

FIG. 3 is a cross-sectional view showing another example of a configuration of the second optical system 40 of FIG. 1. The following description focuses on the differences between the second optical system 40 of FIG. 3 and the second optical system 40 of FIG. 2A. Like reference numerals are used to indicate substantially identical elements.

Referring to FIG. 3, the second optical system 40 includes a second grating 40*h* at the position of the first grating 40*b* in FIG. 2A. The second grating 40*h* may have a groove density (a slit density) that is different from that of the optical modulator 40*a*. The second grating 40*h* may have a groove density smaller than that of the optical modulator 40*a*, for example, the optical modulator 40*a* may have a groove density of 400 that corresponds to a fourth diffracted light, and the second grating 40*h* may have a diffraction density of approximately 300 which is smaller than that of the optical modulator 40*a*. First and second lenses 40*f* and 40*g* are provided in parallel to each other between the optical modulator 40*a* and the second grating 40*h* to compensate for a difference in groove density (diffraction density) of the optical modulator 40*a* and the second grating 40*h*. The optical modulator 40*a*, the first and second lenses 40*f* and 40*g*, and the second grating 40*h* may constitute a modulation and correction device. The first and second lenses 40*f* and 40*g* may be convex lenses and may have focal lengths that are different from each other. For example, the first lens 40*f* may have a focal length of 30 nm, and the second lens 40*g* may have a focal length of 40 nm. The optical modulator 40*a*, the first lens 40*f*, the second lens 40*g*, and the second grating 40*h* may be arranged on the same optical axis. The first and second lenses 40*f* and 40*g* may be dual side convex lenses, but tare not limited thereto.

Figure 4:
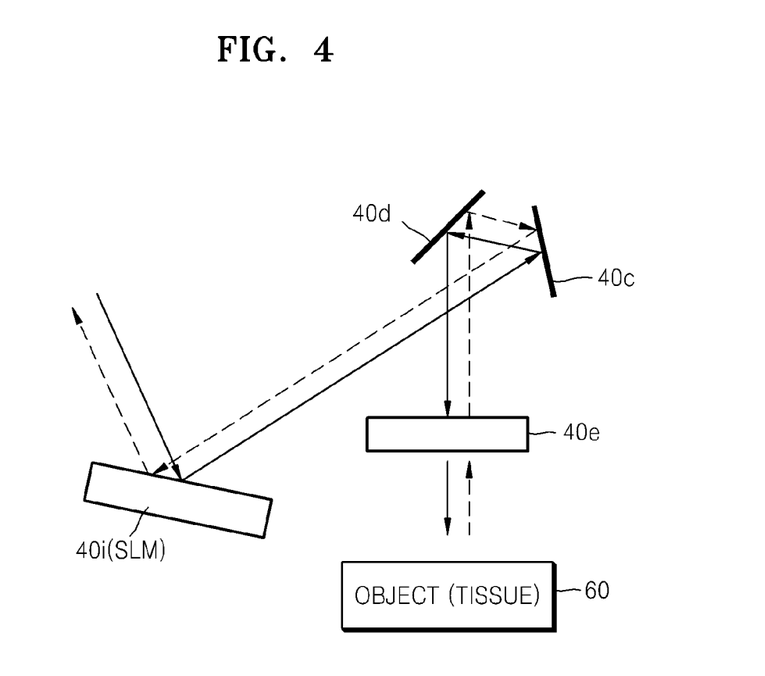
FIG. 4 is a cross-sectional view of another example of a configuration of a second optical system of FIG. 1.

FIG. 4 is a cross-sectional view of another example of a configuration of the second optical system 40 of FIG. 1.

Referring to FIG. 4, the second optical system 40 includes a spatial light modulator (SLM) 40*i*, the first and second mirrors 40*c* and 40*d*, and the first object lens 40*e*. The spatial light modulator 40*i* reflects light (the solid line) that enters from the optical coupler 24 to the first mirror 40*c*. The progress of light after the first mirror 40*c* is the same as the progress described above. After the light is scanned onto the object 60, light (the dashed line) reflected by the object 60 enters the optical coupler 24 via the first object lens 40*e*, the second mirror 40*d*, the first mirror 40*c*, and the spatial light modulator 40*i*.

Figure 5:
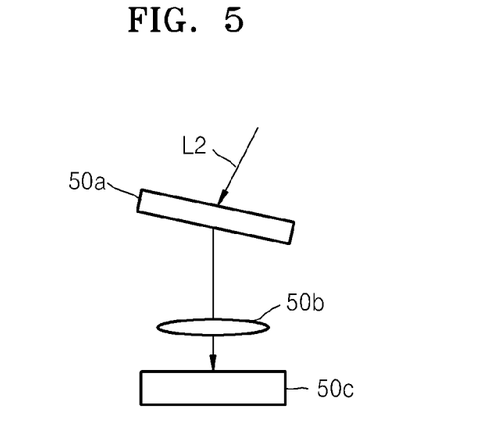
FIG. 5 is a cross-sectional view of an example of a configuration of a third optical system of FIG. 1.

FIG. 5 is a cross-sectional view of an example of a configuration of the third optical system 50 of FIG. 1.

Referring to FIG. 5, the third optical system 50 includes a third grating 50a, a third lens 50b, and an optical image sensing device 50c. Light L2 that enters from the optical coupler 24 includes information of a tomographic image of a given depth of the object 60, and enters the optical image sensing device 50c sequentially through the third grating 50a and the third lens 50b. The third grating 50a may have a slit density of, for example, 1200 lines/mm. The optical image sensing device 50c recognizes a tomographic image included in the light L2, and may be, for example, a charge-coupled device (CCD).

Figure 6:
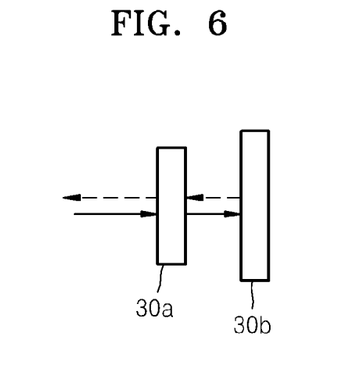
FIG. 6 is a cross-sectional view of an example of a configuration of a first optical system of FIG. 1.

FIG. 6 is a cross-sectional view of an example of a configuration of the first optical system 30 of FIG. 1.

Referring to FIG. 6, the first optical system 30 includes a second object lens 30a and a third mirror 30b which has the same optical axis as the second object lens 30a. The second object lens 30a may be the same object lens 40e of FIG. 2A. Light (the solid line) incident from the optical coupler 24 enters the third mirror 30b through the second object lens 30a. After being reflected by a surface of the third mirror 30b, the light is incident to the optical coupler 24 through the second object lens 30a. An optical path from the optical coupler 24 to the third mirror 30b may be the same as the optical path from the optical coupler 24 to the object 60. Accordingly, a tomographic image corresponding to a predetermined depth of the object 60 may be obtained through an interference pattern of light (a reference light) that is divided with respect to the first optical system 30 and light that is divided with respect to the second optical system 40 to scan the object 60 to a predetermined depth.

Figure 7:
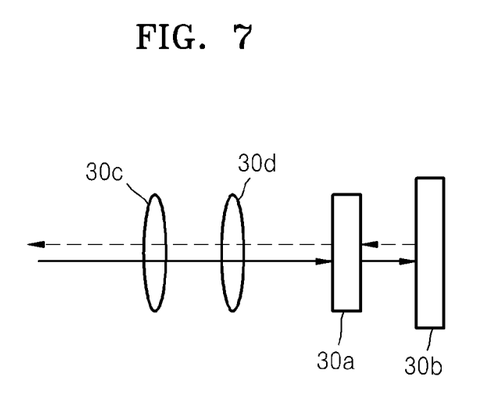
FIG. 7 is a cross-sectional view of another example of a configuration of a first optical system of FIG. 1.

FIG. 7 is a cross-sectional view of another example of a configuration of a first optical system 30 of FIG. 1. The configuration of the first optical system 30 of FIG. 7 corresponds to the second optical system 40 of FIG. 3.

Referring to FIG. 7, the first optical system 30 includes fourth and fifth lenses 30c and 30d which have the same optical axis, a second object lens 30a, and a third mirror 30b. The fourth and fifth lenses 30c and 30d are arranged between the optical coupler 24 and the second object lens 30a. Light (the solid line) that enters from the optical coupler 24 enters a third mirror 30b through the fourth lens 30c, the fifth lens 30d, and the second object lens 30a, and light (the dashed line) reflected by the third mirror 30b enters the optical coupler 24 sequentially through the second object lens 30a, the fifth lens 30d, and the fourth lens 30c.

Figure 8:
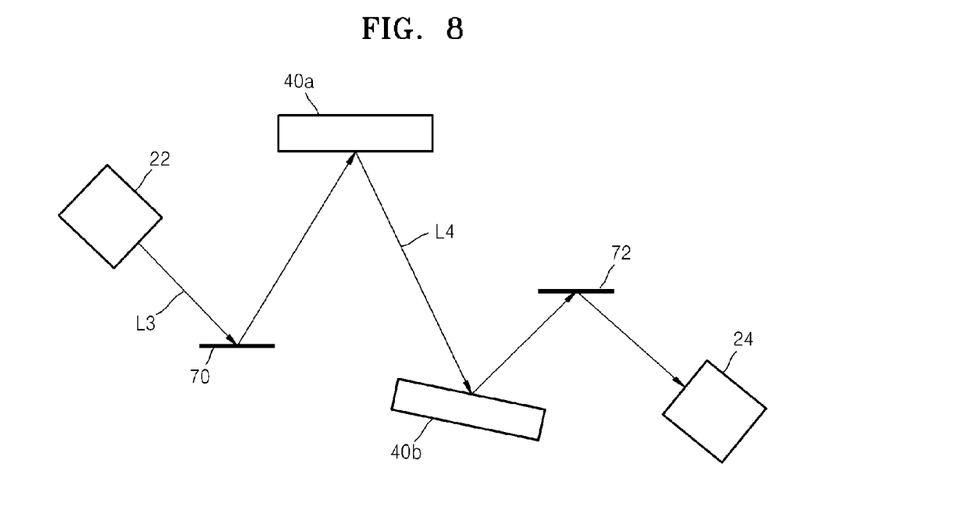
FIGS. 8 and 9 are cross-sectional views showing examples of elements of other examples of a tomographic image generation apparatus.

FIG. 8 is a cross-sectional view showing examples of elements of another example of a tomographic image generation apparatus. The following description focuses on the differences between the apparatus of FIG. 1 and the apparatus of FIG. 8. Like reference numerals are used to denote substantially identical elements.

Referring to FIG. 8, the apparatus includes the modulation and correction device of FIG. 2A, that is, the optical modulator 40a and the first grating 40b, between the optical control unit 22 and the optical coupler 24. In the apparatus, light L3 emitted from the optical control unit 22 is reflected at a fourth mirror 70, and then enters the optical modulator 40a. Light L4 modulated in the optical modulator 40a enters the first grating 40b. The modulated light L4 is reflected at the first grating 40b and enters a fifth mirror 72. The configuration of the second optical system 40 of the apparatus of FIG. 8 may be the same as that of the second optical system 40 of FIG. 2A when the optical modulator 40a and the first grating 40b are removed.

Meanwhile, in FIG. 8, to change an optical path between the optical control unit 22 and the optical modulator 40a, at least one more mirror besides the fourth mirror 70 may be included. That is, at least one mirror besides the fourth mirror 70 may be further included between the optical control unit 22 and the optical modulator 40a.

Also, at least one mirror besides the fifth mirror 72 may be further included between the first grating 40b and the optical coupler 24.

Figure 9:
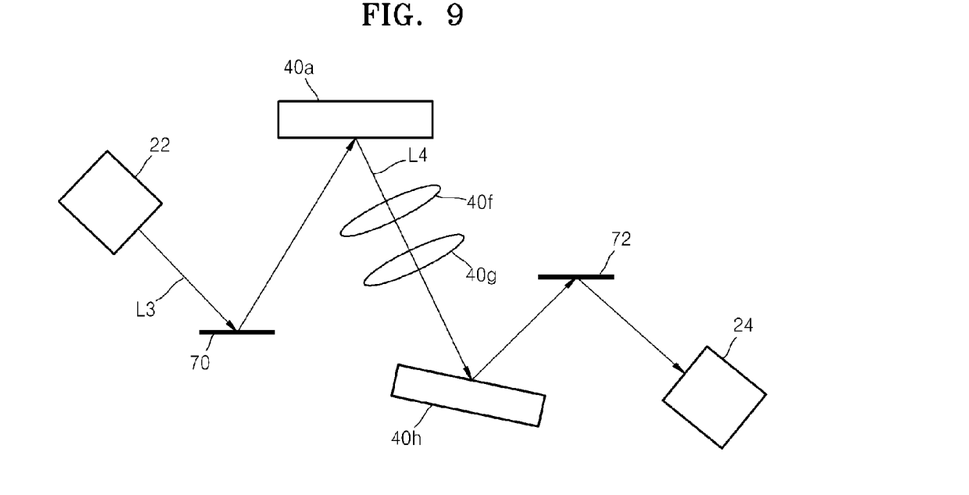

FIG. 9 is a cross-sectional view showing examples of elements of another example of a tomographic image generation apparatus. The following description will focus on the differences between the apparatus of FIG. 1 and the apparatus of FIG. 9. Like reference numerals are used to indicate substantially identical elements.

Referring to FIG. 9, the apparatus includes the fourth and fifth mirrors 70 and 72 between the optical control unit 22 and the optical coupler 24, and includes the modulation and correction device of FIG. 3, that is, the optical modulator 40a, the first and second lenses 40f and 40g, and the second grating 40h, between the fourth and fifth mirrors 70 and 72. Light L3 emitted from the optical control unit 22 is reflected at the fourth mirror 70 and enters the optical modulator 40a. Light L4 modulated at the optical modulator 40a enters the second grating 40h sequentially passing through the first and second lenses 40f and 40g. The light L4 that entered the second grating 40h is reflected at the fifth mirror 72 and enters the optical coupler 24. In the apparatus of FIG. 9, the configuration of the second optical system 40 may be the same as that of the second optical system 40 of FIG. 3 when the optical modulator 40a, the first and second lenses 40f and 40g, and the second grating 40h are removed.

In FIG. 9, to change an optical path between the optical control unit 22 and the optical modulator 40a, at least one more mirror besides the fourth mirror 70 may be included. That is, at least one mirror besides the fourth mirror 70 may be further included between the optical control unit 22 and the optical modulator 40a.

Also, at least one mirror besides the fifth mirror 72 may be further included between the second grating 40h and the optical coupler 24.

Figure 10:
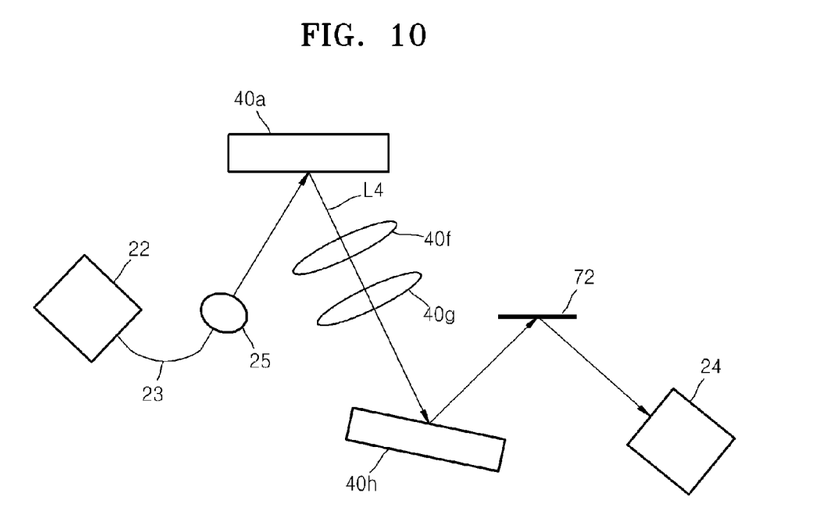
FIG. 10 is a cross-sectional view of an example of a modified version of the configuration of FIG. 9.

FIG. 10 is a cross-sectional view of an example of a modified version of the configuration of FIG. 9.

Referring to FIG. 10, instead of the fourth mirror 70 of FIG. 9, a light source 25 connected to the optical control unit 22 may be used. Light having a plane wave generated from the light source 25 may enter the optical modulator 40a. The optical control unit 22 and the light source 25 may be connected to each other using an optical transmission medium 23, which may be, for example, an optical fiber.

Also, a sixth mirror (not shown) may be included between the fifth mirror 72 and the optical coupler 24. At this point, the sixth mirror may reflect light that is reflected by the fifth mirror 72 to the optical coupler 24. At least one mirror besides the fifth mirror 72 and the sixth mirror may be further included between the second grating 40h and the optical coupler 24.

Figure 11:
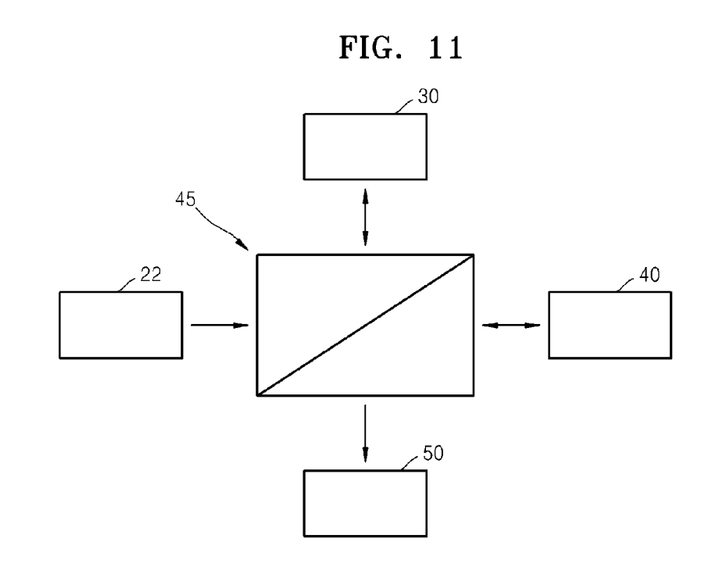
FIG. 11 is a cross-sectional view showing an example of a beam splitter that is used instead of an optical coupler in a tomographic image generation apparatus.

FIG. 11 is a cross-sectional view of an example of a beam splitter 45 that is used instead of the optical coupler 24 in a tomographic image generation apparatus. Light that enters the beam splitter 45 from the optical control unit 22 is divided with respect to the first and second optical systems 30 and 40. Lights that enter the beam splitter 45 from the first and second optical systems 30 and 40 are combined and transmitted to the third optical system 50. Light that is transmitted to the third optical system 50 from the beam splitter 45 may be transmitted by an optical transmission medium such as an optical fiber.

In FIG. 11, a modulation and correction device described with reference to FIGS. 8 through 10 may be included between the optical control unit 22 and the beam splitter 45.

Meanwhile, in the apparatuses of FIGS. 1, 8, and 9, the elements may be spatially separated on the same optical axis, may be connected to each other using an optical transmission medium, or may be configured without an optical transmission medium. The optical transmission medium may be, for example, an optical fiber or a waveguide.

When the elements are configured without an optical transmission medium, the elements are in a spatially separated state arranged on an optical axis. Accordingly, light emitted from an element, for example, the beam splitter 45, may directly enter another element, for example, the second optical system 40.

In the examples described above, a tomographic image generation apparatus may be an optical coherence tomography apparatus or an optical coherence tomography microscope.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A tomographic image generation apparatus comprising:
a light source unit configured to emit light to be used for scanning an object;
an optical control unit configured to control a direction of propagation of light;
an optical coupler configured to divide and combine incident light;
a plurality of optical systems optically connected to the optical coupler; and
a modulation and correction device comprising an optical modulator and configured to modulate and correct the light to be used for scanning the object;
wherein in the optical modulator, a reflection region of light that enters from the optical coupler is different from a reflection region of light that enters from the object.

2. The tomographic image generation apparatus of claim 1, wherein the modulation and correction device is disposed between the optical control unit and the optical coupler.

3. The tomographic image generation apparatus of claim 1, wherein the plurality of optical systems comprise:
a first optical system configured to provide a reference light; and
a second optical system configured to irradiate light to the object.

4. The tomographic image generation apparatus of claim 3, wherein the plurality of optical systems further comprise a third optical system configured to receive an interference pattern, the interference pattern generated by light generated from the first optical system and light generated from the second optical system.

5. The tomographic image generation apparatus of claim 3, wherein the second optical system comprises the modulation and correction device.

6. The tomographic image generation apparatus of claim 3, wherein the second optical system comprises:
a spatial light modulator (SLM) configured to modulate light that enters from the optical coupler;
a galvanometer configured to reflect light that enters from the SLM to the object and reflect light that enters from the object to the SLM; and
an object lens configured to focus light that enters from the galvanometer onto the object.

7. The tomographic image generation apparatus of claim 6, wherein the modulation and correction device is disposed between the second optical system and the optical coupler.

8. The tomographic image generation apparatus of claim 3, wherein the modulation and correction device is disposed between the optical coupler and the second optical system.

9. The tomographic image generation apparatus of claim 1, wherein the modulation and correction device comprises:
the optical modulator, configured to modulate only light that enters from the optical coupler; and
a grating configured to offset diffracted light unnecessarily generated in the optical modulator.

10. The tomographic image generation apparatus of claim 9, wherein the optical modulator corresponds to a first grating having a plurality of grooves and the grating has a groove density that is the same as a groove density of the first grating.

11. The tomographic image generation apparatus of claim 9, wherein the optical modulator corresponds to a first grating having a plurality of grooves and the grating has a groove density that is different than a groove density of the first grating; and
the modulation and correction device further comprises a first lens and a second lens disposed between the first grating and the grating and configured to compensate for the difference in groove density between the first grating and the grating.

12. The tomographic image generation apparatus of claim 9, wherein the optical modulator is a digital micro-mirror device (DMD) or a spatial light modulator (SLM).

13. The tomographic image generation apparatus of claim 1, wherein the modulation and correction device comprises:
the optical modulator, configured to modulate light that enters from the optical coupler; and
a grating configured to offset diffracted light unnecessarily generated from the optical modulator.

14. The tomographic image generation apparatus of claim 13, wherein the optical modulator corresponds to a first grating having a plurality of grooves and the grating has a groove density that is different from a groove density of the first grating; and
the modulation and correction device further comprises a first lens and a second lens disposed between the first grating and the grating and configured to compensate for the difference in groove density between the first grating and the grating.

15. The tomographic image generation apparatus of claim 14, wherein the first optical system comprises two lenses corresponding to the first and second lenses.

16. The tomographic image generation apparatus of claim 1, wherein the modulation and correction device is disposed between the optical coupler and the object.

17. The tomographic image generation apparatus of claim 1, wherein the tomographic image generation apparatus is an optical coherence tomography apparatus or an optical coherence tomography microscope.

18. A method of operating a tomographic image generation apparatus, the method comprising:
- emitting light from a light source to be used for scanning an object;
- controlling a direction of propagation of light using an optical control unit;
- dividing and combining incident light through an optical coupler;
- modulating and correcting, using a modulation and correction device comprising an optical modulator, the light to be used for scanning the object; and
- performing an optical modulation operation with respect to only light that is reflected to the object using the optical modulator of the modulation and correction device,
- wherein in the optical modulator, a reflection region of light that enters from the optical coupler is different from a reflection region of light that enters from the object.

19. The method of claim 18, wherein
- the light that enters the optical modulator from the optical coupler is incident to a first region of the optical modulator;
- the light that enters the optical modulator from the object is incident to a second region of the optical modulator;
- the first and second regions are separated from each other; and
- an optical modulation operation is performed only in the first region.

20. The method of claim 18, further comprising performing the modulating and correcting between the optical control unit and the optical coupler.

21. The method of claim 18, further comprising performing the modulating and correcting between the optical coupler and the object.

22. The method of claim 18, further comprising configuring the tomographic image generation apparatus to comprise a beam splitter instead of the optical coupler.

* * * * *